United States Patent [19]

Tumlinson, III et al.

[11] 4,179,446
[45] Dec. 18, 1979

[54] SEX PHEROMONE PRODUCED BY THE FEMALE JAPANESE BEETLE: SPECIFICITY OF MALE RESPONSE TO ENANTIOMERS

[75] Inventors: James H. Tumlinson, III, Gainesville, Fla.; Michael G. Klein, Wooster, Ohio; Robert E. Doolittle, Gainesville, Fla.; Thyril L. Ladd, Jr., Wooster, Ohio

[73] Assignee: The United States of America as represented by the Secretary of Agriculture, Washington, D.C.

[21] Appl. No.: 932,079

[22] Filed: Aug. 8, 1978

[51] Int. Cl.$^2$ .................................... C07D 307/32
[52] U.S. Cl. ............................ 260/343.6; 424/84
[58] Field of Search ................................ 260/343.6

[56] References Cited

U.S. PATENT DOCUMENTS 3,342,838  9/1967  Noyori et al. ................. 260/343.6
3,761,584  9/1973  McGovern et al. .................. 424/84

OTHER PUBLICATIONS

Ladd, Jr., J. Econ. Entomol. 63, 905–908 (1970).
Goonewardene, H., J. Econ. Entomol. 63, 1001–1003 (1970).
McGovern et al., J. Econ. Entomol. 63, 1727–1729 (1970).
Klein et al., Environ. Entomol. 1, 397–399 (1972).
McGovern et al., J. Econ. Entomol. 69, 468–470 (1976).
Klein et al., J. Econ. Entomol. 66, 373–374 (1973).
Chem. Abstracts 84:135060z.
Chem. Abstracts, 87:22434t.
Chem. Abstracts 74:61984y.
Ravid et al., Tetrahedron Letters, 5, 423–426 (1977).
Schwarze, Nature, 223, 525–526 (Aug. 1969).
Haverkamp et al., Recueil 87, 1335 (1968), p. 1339 pertinent.

Primary Examiner—Ethel G. Love
Attorney, Agent, or Firm—M. Howard Silverstein; David G. McConnell; Raymond C. Von Bodungen

[57] ABSTRACT

(Z)-5-(1-decenyl)dihydro-2(3H)-furanone, isolated from virgin female Japanese beetles, *Popilla Japonica*, attracted males of the species in field bioassays. However, the synthesized racemic mixture of this compound did not attract male Japanese beetles. The Z- and E-isomers and the saturated analog of both enantiomers of this compound were synthesized stereospecifically. Pure synthetic (R,Z)-5-(1-decenyl)dihydro-2(3H)-furanone was competitive with live females and with the pheromone isolated from live females in attracting males. Male response was strongly inhibited by small amounts of the (S,Z)-isomer.

2 Claims, 1 Drawing Figure

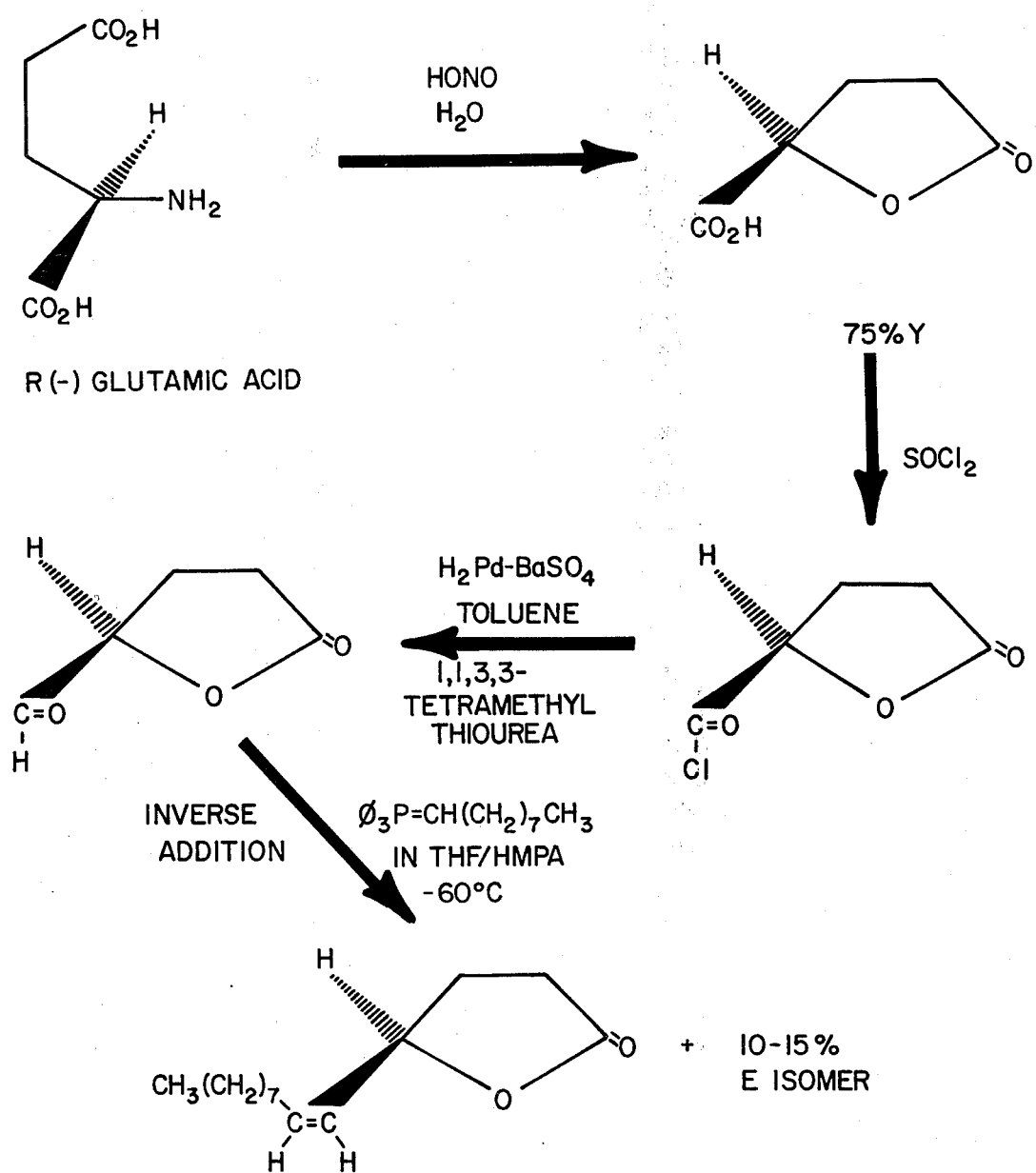
FIGURE I

16
SEX PHEROMONE PRODUCED BY THE FEMALE JAPANESE BEETLE: SPECIFICITY OF MALE RESPONSE TO ENANTIOMERS

BACKGROUND OF THE INVENTION (1) Field of the Invention:

This invention relates to a new composition of matter and the process for making same. A synthetic sex attractant, (R,Z)-5-(1-decenyl)dihydro-2(3H)-furanone has been synthesized and has been found attractive to male Japanese beetles, *Popilla japonica.*

(2) Abstract of the Prior Art

The Japanese beetle, *Popilla japonica* (Coleoptera: Scarabaeidae), was introduced to North America about 1916 and has since become well established in the eastern part of the United States. The adults are devastating pests of a variety of trees, ornamentals, and cultivated crops, and the larvae attack the roots of grasses.

The synthesized pheromone, (R,Z)-5-(1-decenyl)-dihydro-2(3H)-furanone (FIG. 1), was very attractive to male Japanese beetles in field tests, but a racemic mixture of the synthesized Z-isomer was inactive. Several pheromones that contain asymetric carbons have previously been identified, and in many instances only one enantiomer elicits a behavioral response. On the other hand, Borden et al, Science 192, 894 (1976), reported that both enantiomers of 6-methyl-5-hepten-2-01 were necessary to attract *Gnathotrichus sulcatus,* and Wood et al, Ibid, 192, 896, reported that *Dendroctonus brevicomis* responded to specific enantiomers of exo-brevicomin and frontalin. However, this is the first report of inhibition of a behavioral response to a pheromone by its enantiomer.

SUMMARY OF THE INVENTION

This invention provides a method for synthesizing (R,Z)-5-(1-decenyl)dihydro-2(3H)-furanone useful as a sex attractant for the Japanese male beetles.

DESCRIPTION OF THE PREFERRED EMBODIMENTS

The invention described herein has been shown to attract male Japanese beetles.

In replicated field tests traps baited with 5 μg of the pure synthesized pheromone (the (R,Z)-isomer) captured about twice as many males as traps baited with 4 virgin females. However, admixture of as little as 1% of the synthesized (S,Z)-isomer significantly reduced the response of males to the (R,Z)-isomer. Although females contain smaller amounts of the E-isomer and the saturated analog of the pheromone (see later), the role of these compounds could not be determined in our tests.

Smith and Hadley, The Japanese beetle, USDA Circ. 363, 67p (1926), first reported that large numbers of searching male Japanese beetles were attracted to emerging females. Later, Ladd, *J. Econ. Entomol,* 63, 905 (1970), demonstrated that single virgin female beetles emitted a volatile sex pheromone and that traps baited with virgin females captured large numbers of males. We obtained a benzene solution highly attractive to males in field bioassays by rinsing the glass vessels used to hold virgin females. The bioassays were conducted by pouring 50 to 100 female-day equivalents (FD) of the benzene wash into a glass petri dish placed on the ground in an open field or golf course fairway. The number of males responding in 5 min. was counted and compared with the number responding to 3 females in a small cage in the same area during the same period. At least 3 replicates of each test were run, and all steps in the isolation procedure were monitored with this assay.

The benzene wash was filtered to remove solids and concentrated by vacuum distillation (150 mm, 36° C.) through a 10-cm Vigreaux column: The concentrated benzene wash (50 FD) was as attractive to males as 3 virgin females. It was fractionated by gel permeation liquid chromatography with hexane as the mobile phase, and the hexane was removed from the active fraction by distillation at atmospheric pressure through a 10-cm Vigreaux column. Neither distillate was active. The concentrated liquid chromatographic fraction was then purified by sequential gas chromatography on OV-101, Carbowax 20 M, SP 2300, SP 2340, and finally a second Carbowax 20 M column. One compound was obtained from the final carbowax 20 M column that contained all the activity of the original flask wash and was greater than 99% pure when rechromatographed on all of the columns.

The active compound was identified by mass, infrared, and nmr spectroscopy and by chemical transformations. The methane ionization mas spectrum of the pheromone had the following diagnostic peaks: $(M+1)$, 225; $(M-1)$, 223; $(M+29)$, 253; $(M+41)$, 265; $[(M+1)-18]$, 207; $[(M+1)-36]$, 189; $[(M+1)-60]$, 165; and a typical straight chain, unsaturated hydrocarbon series of peak clusters from m/e 67 to 169. The infrared spectrum (10) obtained with about 25 μg of pure pheromone showed strong absorptions at 1790 cm$^{-1}$ (C=O). The remainder of the infrared spectrum consisted of hydrocarbon and olefinic absorption bands. A band at 980 cm$^{-1}$ suggested that a trans olefinic bond might be present though it was much weaker than would be expected. This evidence suggested a γ-lactone of a 14 carbon hydroxy acid with one double bond, and this was supported by the nmr spectrum (CCl$_4$, internal tetramethylsilane standard, δ, ppm): 0.87, triplet, 3H [CH$_3$]; 1.27 broad singlet, about 14H [—(CH$_2$)$_7$—]; 2.06-2.42, broad multiplet, 4–5H [ring protons]; and multiplets at 5.06, 1H, and 5.46, 1H [olefinic].

Microozonolysis (11) of the pure pheromone in carbon disulfide at $-78°$ C., reductive cleavage of the ozonide with triphenylphosphine, and gas chromatography of the product on OV-101 yielded one major peak that was identical in retention time and mass spectrum to nonanal. Thus, the pheromone was tentatively identified as (Z)- or (E)-5-(1-decenyl)dihydro-2(3H)-furanone.

Racemic (Z)- and (E)-5-(1-decenyl)dihydro-2(3H)-furanone were synthesized by the addition of the lithium salt of 1-decyne to methyl 4-oxo butyrate. The γ-lactone was formed in the course of this reaction, and the resulting acetylenic lactone was reduced to the olefinic and saturated lactones. The Z-, and E-, and saturated lactones were purified by high resolution, high pressure liquid chromatography on silic with hexane-diethyl ether mobile phase and by gas chromatography on OV-101 and Carbowax 20 M. The resulting synthetic lactones were greater than 99.5% pure when analyzed on all 5 gas chromatographic columns used in this investigation. The synthesized racemic (Z)-5-(1-decenyl)dihydro-2(3H)-furanone had a retention time identical to that of the natural pheromone on all 5 gas chromatographic columns, had the same mass, nmr, and infrared spectra, and gave the same ozonolysis product. Additionally, the synthesized racemic saturated lactone was identical in every respect to another compound obtained from females and eluted just prior to the pheromone on the SP2340 column. Similarly, the synthesized racemic E-lactone was identical in GC retention times on all 5 columns, in mass spectra, and in the ozonolysis product to a third compound from the female Japanese beetle that eluted just after the pheromone in the final Carbowax 20 M column. The saturated analog and the E-isomer amounted to about 3 and 15 percent, respectively, of the Z-isomer (the pheromone) in the material obtained from females.

Samples containing 5, 50, 500, and 5000 ng of the pure synthesized racemic Z-isomer dissolved in 0.25 μl of hexane were dioassayed; all failed to attract male beetles to the petri dish. In some instances males appeared to orient and fly upwind toward the synthesized lactone, but they always stopped 30 cm or more from the petri dish. Admixture of 10, 13, 15, 17, and 20% of the E isomer to the Z isomer also failed to produce a response equivalent to that elicited by 10 to 20 ng of the pheromone isolated from females. However, 1 to 3 occasionally moved closer and crawled into the petri dishes baited with 85/15 or 83/17 mixtures of the Z/E-isomers. In the same test, 4 females or 100 FD of the pheromone isolated from females attracted 20 to 40 males that moved into the petri dish. In a similar test admixture of 3 to 7% of the saturated lactone to the Z/E mixtures failed to elicit a response from males.

During these tests we noted that the synthetic racemic olefinic lactones inhibited the response of males to virgin females. Although 5 ng of the Z-isomer failed to inhibit response, the addition of 50 to 5000 ng of the Z-isomer to a petri dish containing a cage of 3 virgin females reduced the response of males to females by 80 to 100 percent. The E-isomer was an effective inhibitor only at the 5000-ng level.

Since the purity of the natural pheromone and the synthesized lactone had been rigorously examined by GC, spectroscopic, and chemical methods and since the two compounds were identical chemically, the most likely explanation for the lack of activity of the synthesized material seemed to be inhibition of attraction by one of the enantiomers in the synthetic racemic mixture. Insufficient material was available to determine the optical rotation of the natural pheromone so we synthesized both enantiomers stereospecifically. The synthesis route for the R-enantiomer is given in FIG. 1. The S-enantiomer was synthesized by the same method starting with S(+)-glumatic acid. The Z- and E-isomers of each synthesized enantiomer were obtained in greater than 99% purity by liquid chromatography on silica and gas chromatography on Carbowax 20 M. The optical rotations of the (R,Z)- and (S,Z)-enantiomers were $[\alpha]_D^{26°} = -69.6°$ and $[\alpha]_D^{26°} = +70.5°$, respectively. The Z-enantiomers were identical chromatographically, spectroscopically, and chemically to the natural pheromone.

Samples of 5, 50, and 500 ng and 5, 50, and 500 μg of the (R,Z)-, (R,E)-, and R-saturated and the (S,E)-, and S-saturated isomers were dioassayed in the field near Wilmington, N.C. in June 1976 and near Wooster, Ohio, in July 1976. (R,Z)-5-(1-decenyl)dihydro-2(3H)-furanone was very attractive to male Japanese beetles. A 50-ng sample of the (R,Z)-isomer was about equal to 4 virgin females in the bioassay. Traps (3) baited with 5 μg of the (R,Z)-isomer attracted twice as many males in 1 day as traps batied with 4 virgin females (Table 1). In replicated tests, traps baited with 50 and 500 ng of the (R,Z)-isomer caught more males than traps baited with equivalent amounts of the natural pheromone.

When traps were baited with the other 5 isomers, only the (R,E)-isomer attracted male Japanese beetles, and the captures, while significantly greater than those captured by an empty trap, were only about 10% of those in traps baited with the (R,Z)-isomer. However, admixture of 10, 15, or 20% of the (R,E)- with the (R,Z)-isomer did not significantly increase trap captures over those of the pure (R,Z)-isomer (Table 1). Similarly admixture of 2, 4, 6, 8, 10, and 20% of the R-saturated analog to the pure (R,Z)-isomer or to a mixture of the (R,Z)- and (R,E)-isomer did not significantly increase trap captures (Table 2).

Since the racemic mixture of the snythesized pheromone was inactive, we prepared mixtures of the (R,Z), and (S,Z) entantiomers in which the (S,Z) enantiomer amounted to 0.5, 1, 2, 5, 10, 20, and 50% of the total mixture. The amount of (R,Z)-enantiomer was held constant at 5 μg in each mixture. In replicated field tests as little as 1% of the (S,Z)-enantiomer significantly reduced the number of males captured by traps baited with the pure (R,Z)-enantiomer and the number of males captured generally decreased with increasing quantities of the (S,Z)-enantiomer (Table 3). Considerably less than 50% of the (S,Z)-enantiomer was required to reduce trap captures to the level of an empty trap. This correlates well with our previous findings that the racemic mixture of the Z isomer did not attract males.

It is unusual in Coleoptera to find a pheromone consisting of only one compound, and inhibition of response to a pheromone by its enantiomer is unique among pheromones reported thus far. Careful investigation of the material obtained from females revealed no synergists through the E- and saturated isomers were present in smaller amounts. We can speculate that these isomers were present in smaller amounts. We can speculate that these isomers have some subtle undetected role in the chemical communication of this species or that they play a role in species isolation in the beetle's native habitat. Synthesized (R,Z)-5-(1-decenyl)dihydro-2(3H)-furanone is a potent attractant for male Japanese beetles and appears to have considerable potential for survey and control of this serious pest.

The following examples illustrate but do not limit the scope of this invention.

EXAMPLE 1

Preparation of

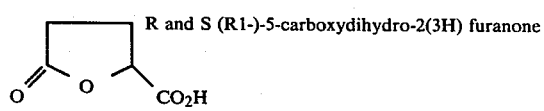

R and S (R1-)-5-carboxydihydro-2(3H) furanone

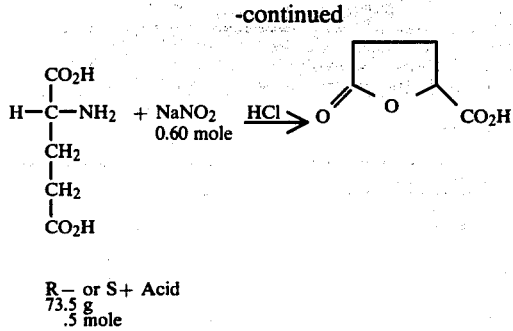

R- or S+ Acid
73.5 g
.5 mole

The glutamic acid is suspended with stirring in 250 cc of H₂O and cooled to about 20° C. Then the sodium nitrite (45 g; 0.60 mole) dissolved in 150 cc of H₂O was added simultaneously with 300 ml of 2NHcl (0.60 mole) keeping the temperature at 15°–18° C. After addition, the mixture was allowed to stir at room temperature overnight. The water is removed by evaporation at <40° C. The oily solid residue is extracted with acetone at room temperature and the inorganic salts removed by filtration and washed with acetone. The filtrate was concentrated to 250 ml (anhydrous sodium sulfate was added) and allowed to stand in the refrigerator overnight. The salts were again removed by filtration and the solvent evaporated.

The oily residue was taken up in ethyl acetate and any insoluble material removed by filtration. The solvent was evaporated and the residual oil vacuum distilled bp 160°–170°/0.05 mm. The distilled product was dissolved in the minimum amount of warm ethyl acetate, an equal volume of benzene was added and when the mixture cooled to room temperature a seed crystal was added and the product crystallized. The mp is 72°–74° C. and the yield around 70–80%. The product can be dried in a vacuum oven at room temperature over P₂O₅.

EXAMPLE 2

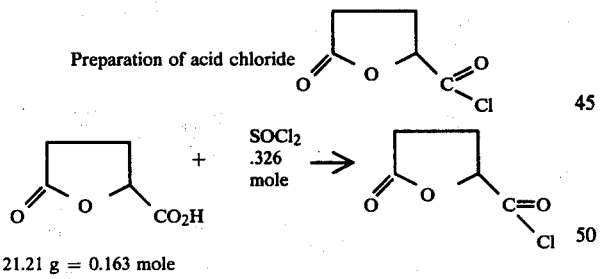

Preparation of acid chloride 21.21 g = 0.163 mole

The acid was heated with thionyl chloride (0.326 mole; 38.79 g, 23.68 ml, Aldrich 15,780-5) in a water bath at 85° for three hours under a reflux condenser fitted with a drying tube and then allowed to stand at room temperature overnight. The excess thionyl chloride is removed under aspirator vacuum and by evaporation several times with anhydrous ether. The residual oil was vacuum distilled bp 80°–85°/0.5 mm to give a slightly yellow oil, 21.67 g 89.5%. Alternatively, the acid chloride can be prepared by heating 21.21 g (0.163 mole) of lactone acid with a mixture of water bath at 60°–70° C. for 5 hours. The benzene and excess oxalyl chloride was removed under water aspirator and the residual oil is vacuum distilled to give 23.19 g (96%) of a clear oil b.p. 76°–84°/0.2 mm. The acid chloride prepared in this fashion is of higher purity (less sulfur residues) than that from thionyl chloride, but the effect of these impurities on the next reaction in the sequence is not clear.

EXAMPLE 3

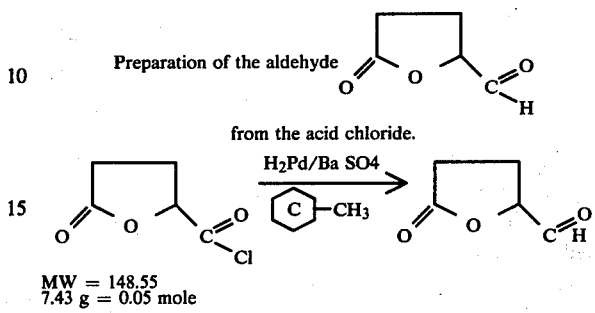

Preparation of the aldehyde from the acid chloride.

MW = 148.55
7.43 g = 0.05 mole

The reaction was run in a 500-ml 3 neck flask fitted with a mercury sealed mechanical stirrer, condenser, and gas dispersion tube. The catalyst (prepared according to Org. Synthesis Vol. 3, p. 685, commercial palladium on barium sulfate from Englehard might be usable in this reaction) and 200 ml of toluene (distilled from Na) were placed in the clean dry N₂ swept flask. Hydrogen gas was passed through the mixture for ½ hour and then the acid chloride was added and the mixture was heated to 69°–65° C. in an oil bath with rapid stirring. The evolution of hydrogen chloride was monitored by passing the effluent gasses through water and titrating the Hcl with 5 N sodium hydroxide. It should take about 10 ml of base to neutralize the Hcl from 0.05 mole of acid chloride. It took about 5 hours for this evolution. After the reaction was over, the mixture was cooled and the catalyst removed by filtration through filter-aid. The residual viscous liquid containing entrained catalyst was titrated with methylene chloride and the catalyst removed by filtration. The filtrate is concentrated to give 4.0 g (0.035 mole 70%) of a viscous oil that is used directly in the next step with no further purification. Attempts at purification of this aldehyde by distillation resulted in decomposition and the material resisted all efforts at crystallization. It was therefore used in the crude form for the next step.

EXAMPLE 4

Conversion of the aldehyde to a Z,E mixture of

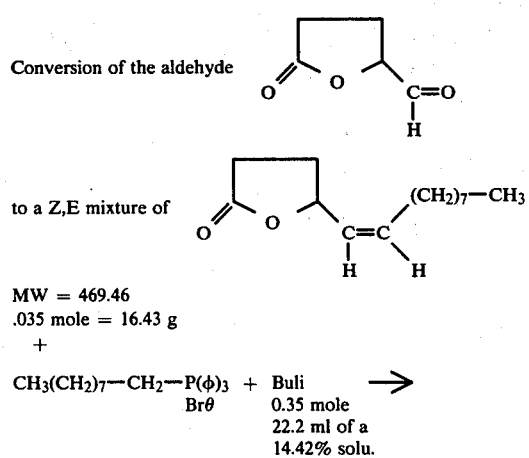

MW = 469.46
.035 mole = 16.43 g
+

CH₃(CH₂)₇—CH₂—P(φ)₃ + BuLi →
            Brθ        0.35 mole
                       22.2 ml of a
                       14.42% solu.

-continued

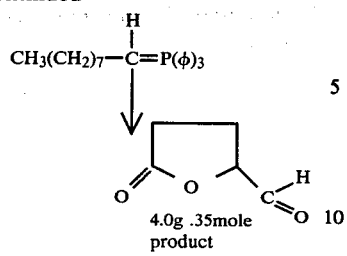

4.0g .35mole product

The ylide was prepared in a 250-ml 4-neck flask fitted with a thermometer, magnetic stirrer, 25 ml dropping funnel and a septum stopper. The phosphosium salt was weighed out in a dry box and placed in the clean, dry $N_2$ swept flask. The contents of the flask are kept under an atmosphere of $N_2$ and 60 ml of dry tetrahydrofuran was added and the mixture was stirred until the salt dissolved. The contents of the flask were cooled to $-5°$ C. and the butyl lithium was added dropwise at such a rate as to keep the temperature below $+5°$. After addition of the Buli, the flask was held at 0° C. for one hour.

The aldehyde was dissolved in a mixture of 15 ml of THF and 15 ml of hexamethylphosphoramide and transferred to a 250-ml 3-neck round bottom flask fitted with a thermometer, magnetic stirrer and 125 ml dropping funnel. The aldehyde solvent mixture was cooled to $-50°$ (dry-ice isopropanol bath) and ylide was transferred to the dropping funnel with $N_2$ and added dropwise to the aldehyde HMPA mixture at or below $-35°$ C. until the red color of the ylide persisted in the mixture. The reaction mixture was allowed to rise at room temperature overnight. The reaction was worked up by dilution with ice and water and extraction with ether several times. The ether extracts were washed with water, saturated salt solution, and dried over sodium sulfate. The crude product was passed through a column of silica gel. The product was eluted with hexane and 10% ether/hexane. After removal of the solvent the product was vacuum distilled to give 3.36 g of product (42%) b.p. 110°/0.005 mm. the Z:E ratio was 9:1 by GC analysis on carbowax. Using less polar solvents in place of HMPA lowers the Z:E ratio to about 2:1 for a mixture of ether and methylene chloride.

The attractant is produced when R⊖(D) glutamic acid is used as the starting material whereas the inhibitor is produced when S+(L) glutamic acid is used as the starting material.

Table 1

Male Japanese beetles captured in Ellisco traps baited with mixtures of synthesized (R,Z)- and (R,E)-5-(1-decenyl) dihydro-2(3H)-furanone. Wooster, Ohio, July 1976.

| Ratio[a] RZ/RE | Mean number of males captured[b] (5 replicates) |
|---|---|
| 100/0 | 845 a |
| 90/10 | 981 a |
| 85/15 | 825 a |
| 80/20 | 926 a |
| 4 females | 442 b |

Table 1-continued

Male Japanese beetles captured in Ellisco traps baited with mixtures of synthesized (R,Z)- and (R,E)-5-(1-decenyl) dihydro-2(3H)-furanone. Wooster, Ohio, July 1976.

| Ratio[a] RZ/RE | Mean number of males captured[b] (5 replicates) |
|---|---|
| Empty trap | 26 c |

[a]The quantity of the (R,Z)-isomer was held constant at 5 μg. [b]Means followed by unlike letters differ significantly at the 5% level of probability (Duncan's multiple range test).

Table 2

Male Japanese beetles captured in Ellisco traps baited with mixtures of synthesized (R,Z)-, and (R,E)-5-(1-decenyl) dihydro-2(3H)-furanone and the R-saturated analog. Wooster, Ohio, July 1976.

| Ratio[a] RA/RE/R-Sat | Mean number of males captured[b] (7 replicates) |
|---|---|
| 100/0/0 | 69 bc |
| 98/0/2 | 90 bc |
| 96/0/4 | 108 c |
| 94/0/6 | 57 b |
| 92/0/8 | 90 bc |
| 90/0/10 | 68 bc |
| 80/0/20 | 52 b |
| 85/15/2 | 58 b |
| 85/15/4 | 63 b |
| 85/15/6 | 53 b |
| 85/15/8 | 58 b |
| 85/15/10 | 62 b |
| 0/0/100 | 6 a |
| Empty trap | 3 a |

[a]The quantity of the (R,Z)-isomer was held constant at 500 ng. [b]Means followed by unlike letters differ significantly at the 5% level of probability (Duncan's multiple range test).

Table 3

Male Japanese beatles captured in traps baited with mixtures of synthesized (R,Z)- and (S,Z)-5-(1-decenyl) dihydro-2(3H)-furanone. Wooster, Ohio, July 1976.

| Ratio[a] RZ/SZ | Mean number of males captured[b] (6 replicates) |
|---|---|
| 100/0 | 168 a |
| 99.5/0.5 | 106 ab |
| 99/1 | 91 bc |
| 98/2 | 96 bc |
| 95/5 | 52 bcd |
| 90/10 | 30 cd |
| 80/20 | 9 d |
| 50/50 | 6 d |
| Empty trap | 4 d |

[a]The quantity of the (R,Z)-enantiomer was held constant at 5 μg. [b]Means followed by unlike letters differ significantly at the 5% level of probability (Duncan's multiple range test).

We claim:
1. A process for preparing (R,Z)-5-(1-decenyl)dihydro-2-(3H)-furanone comprising:
   (a) deaminating R(−)glutamic acid by reacting it with sodium nitrate to produce R(−)5-carboxydihydro-2(3H) furanone;
   (b) heating the R(−)-5-carboxydihydro-2(3H)furanone with thionyl chloride to produce the acid chloride from (b);
   (c) reducing the acid chloride from (b) to the corresponding aldehyde;
   (d) reacting the aldehyde from (c) with ylide generated with butyl lithium from nonyltriphenyl-phosphorium bromide to produce a mixture of the Z- and E-isomers of the pheromone (R,Z)-5-(1-decenyl)dihydro-2(3H) furanone; and
   (e) separating the Z isomer from the E isomer by liquid chromatography.

2. The compound (R,Z)-5-(1-decenyl)dihydro-2(3H)-furanone.

* * * * *